United States Patent [19]

Dubrow

[11] Patent Number: 5,164,055
[45] Date of Patent: Nov. 17, 1992

[54] HIGH-VISCOSITY POLYMER MATRIX AND METHODS

[75] Inventor: Robert S. Dubrow, San Carlos, Calif.

[73] Assignee: Applied Biosystems, Inc., Foster City, Calif.

[21] Appl. No.: 472,045

[22] Filed: Jan. 29, 1990

[51] Int. Cl.[5] .................... G01N 27/26; B01D 57/02
[52] U.S. Cl. ........................ 204/180.1; 204/299 R; 204/182.8; 204/183.2
[58] Field of Search ............ 204/299 R, 180.1, 183.2, 204/182.8, 182.9

[56] References Cited

PUBLICATIONS

S. Hjerten et al "High-Performance Electrophoresis of Acidic and Basic Low-Molecular-Weight Compounds and Proteins in the Presence of Polymers and Neutral Surfactants" Journal of Liquid Chromatography, 12(13) 2471-2499 [1989].
N. A. Guzman et al "Capillary Electrophoresis: A New Era in Microseparations" BioPharm Jan. 1989 pp. 22-37.
S. W. Compton & R. G. Brownlee "Capillary Electrophoresis" Biotechniques, vol. 6 No. 5 (1988) pp. 432-440.
D. Tietz et al "Electrophoresis on uncrosslinked polyacrylamide: Molecular sieving and its potential applications" Electrophoresis, 7 (1986) 217-220.
B. J. Radola "Ultra-thin-layer isoelectric focusing" in Electrophoretic Techniques, Simpson & Whittaker, eds. (1983) 106-109.

*Primary Examiner*—John Niebling
*Assistant Examiner*—John S. Starsiak, Jr.
*Attorney, Agent, or Firm*—Joseph A. Smith; Peter J. Dehlinger

[57] ABSTRACT

A supported, substantially uniform matrix for use in electric field-induced separation of molecular components in a sample. The matrix is prepared by forming a viscoelastic polymer matrix and pumping the matrix into a capillary or preparative-scale tube. The polymer type, concentration, and molecular weight are selected to optimize separation of protein or nucleic acid components. The matrix can be expelled from the tube, after fractionation, for analysis and/or recovery of fractionated components.

17 Claims, 7 Drawing Sheets

HIGH-VISCOSITY POLYMER MATRIX AND METHODS

1. FIELD OF THE INVENTION

The present invention relates to separation of molecular components, and in particular, to a flowable, high-viscosity electrophoretic matrix effective as an separation medium for electrophoresis and isoelectric focusing.

2. REFERENCES

Cohen, A. S., et al, Anal Chem, 59:1021 (1987).
Cohen, A. S., et al, J. Chromatography, 458:323 (1988).
Compton, S. w., et al BioTechniques, 6(5):432 (1988).
Kaspar, T. J., et al, J Chromatography, 458:303 (1988).
Lauer, H. H., Anal Chem, 58:166 (1985).
Maniatis, T., et al, "Molecular Cloning, A Laboratory Manual," Spring Harbor Lake, NY (1982).

3. BACKGROUND OF THE INVENTION: ELECTROPHORESIS

Electrophoresis is widely used for fractionation of a variety of biomolecules, including DNA species, proteins, peptides, and derivatized amino acids. One electrophoretic technique which allows rapid, high-resolution separation is capillary electrophoresis (CE) (Cohen, 1987, 1988, Compton, Kaspar, Lauer). Typically, CE employs fused silica capillary tubes whose inner diameters are between about 50-200 microns, and which can range in length between about 10-100 cm or more.

In the usual electrophoresis procedure, an electrophoresis tube, such as a capillary tube, is filled with a fluid electrophoresis medium, and the fluid medium is crosslinked or temperature-solidified within the tube to form a non-flowable, stabilized separation medium. A sample volume is drawn into or added to one end of the tube, and an electric field is applied across the tube to draw the sample through the medium. Electrophoretic separation within the matrix may be based on molecular size, in the case of nucleic acid species (which have roughly the same charge density), or on a combination of size and charge, in the case of peptides and proteins.

The polymer concentration and/or degree of crosslinking of the separation medium may be varied to provide separation of species over a wide range of molecular weights and charges. For separating nucleic acid fragments greater than about 1,000 bases, for example, one preferred temperature-solidified material is agarose, where the concentration of the agarose may vary from about 0.3%, for separating fragments in the 5-60 kilobase size range, up to about 2%, for separating fragments in the 100-3,000 basepair range (Maniatis). Smaller size fragments, typically less than about 1,000 basepairs, are usually separated in cross-linked polyacrylamide. The concentration of acrylamide polymer can range from about 3.5%, for separating fragments in the 100-1,000 basepair range, up to about 20%, for achieving separation in the size range 10-100 basepairs. For separating proteins, crosslinked polyacrylamide at concentrations between about 3-20 percent are generally suitable. In general, the smaller the molecular species to be fractionated, the higher the concentration of crosslinked polymer.

The resolution obtainable in solidified electrophoresis media of the type described above has been limited, in the case of small molecular weight species, by difficulties in forming a homogeneous, uniform polymer matrix at high polymer concentration within an electrophoresis tube, and especially within a capillary tube. In the usual method for forming a high-concentration solidified matrix in a capillary tube, the gel is produced inside the capillary by mixing the gel precursors (typically including reactive monomers or prepolymers, one or more crosslinking agents, polymerization catalyst, polymerization initiator and other additives that may be useful during the separation process, such as surfactants and denaturizers), filling the capillary with this mixture and allowing the gel to cure within the capillary. Unfortunately, in addition to the gel, this process leaves gel residues that can interfere with the chromatographic separation of sample components and lead to premature breakdown of the gel. Because of the extreme length-to-diameter ratio of capillary 15, these residues are not easily removed from the gel by flow of eluent through the capillary. Indeed, in electrophoresis, there is almost no flow of eluent through the gel. The only species that exhibit significant mobility are the ionic species.

Another problem is that the gel generally shrinks by a few percent volume when it cures, so that the gel tends to pull away from the walls of the capillary. As a result, when the electric field is turned on to push sample ions through the capillary, the gel tends to be pushed along and out of the capillary due to ionic groups associated with the gel. To prevent this, it is common to treat the inside surface of the capillary wall and/or to add to the gel precursor a coupling agent, such as silane, to bond the gel to the capillary wall.

An additional problem is that voids sometimes occur in the gel. Such voids are more readily produced in gels that are bonded to the capillary or column wall because they are prevented from pulling away from the wall as they shrink during curing. These voids present obstacles to the ionic flow and can introduce inhomogeneities in the process that degrade resolution. If such a void extends entirely across the internal diameter of the capillary, there will be a complete break in the current path and electrophoresis will be stopped.

To overcome the above problems, in one gel formation process, a capillary is first filled with the gel precursor. Preferable, the gel precursor is at a reduced temperature that inhibits the chemical reaction that results in the formation of the gel. The capillary is then either heated or exposed to radiation in a narrow zone to cure the gel precursor within that zone. This zone is then moved along the capillary to cur the gel along the entire length of the capillary. By use of this moving zone of curing, the still-mobile gel precursor can flow toward the cured zone to compensate for the shrinkage that occurs during curing. Unfortunately, this moving zone process is a slow process that is difficult to control and that significantly increases the time required to produce a capillary gel.

As another approach, it has been proposed to reduce void formation and gel shrinkage by carrying out the gel crosslinking reaction at high pressure. This approach has been only partially successful in reducing inhomogeneities in the gel, and adds substantially to the cost and complexity of the electrophoresis procedure.

Alternatively, in the case of temperature-solidifying polymers, the polymer is introduced into an electrophoresis tube in a fluid form, then allowed to gel to a solid form by cooling within the gel. This approach, however, has limited application, since polymers, such as agar and agarose, which are known to have the necessary temperature-solidifying setting properties, are not effective for fractionating low molecular weight species, even at high polymer concentrations.

A second limitation associated with crosslinked or temperature solidified matrices is the difficulty in recovering fractionated molecular species within the matrix, after electrophoretic separation. In the case of a preparative-scale electrophoresis tube, the solidified matrix must be carefully separated from the walls of the tube before the matrix can be removed, a procedure which is virtually impossible with capillary tubes. Even after the matrix is removed, and the region of the matrix containing the desired molecular species is identified, the species of interest can be recovered from the matrix region only by a lengthy elution procedure, or by electrophoretic elution.

4. BACKGROUND OF THE INVENTION: ISOELECTRIC FOCUSING

Isoelectric focusing (IEF) is a separation method based on migration of different molecular components to their isoelectric points in a pH gradient. The pH gradient is established by subjecting an ampholyte solution containing a large number of different pKi species to an electric field. Molecular components contained in (or added to the equilibrated ampholyte solution) will then migrate to their isoelectric points along the pH gradient. The components can then be isolated by eluting the gradient and capturing selected eluted fractions.

Although IEF methods are usually carried out in a low-viscosity fluid medium, it is occasionally advantageous to perform the IEF separation in a stabilized matrix. One potential advantage of a stabilized matrix is greater resolution, by eliminating the band spreading that occurs when a fluid medium is eluted from a tube, and by eliminating electroosmotic effects which may be present in capillary IEF. A stabilized separation medium allows use of certain gel analysis techniques, such as gel autoradiography which are not possible with a fluid medium.

Crosslinked or temperature-stabilized gels of the type described above have been employed in IEF methods, but present some of the same limitations noted above for electrophoretic methods. In particular, the stabilized gels are generally not removable from capillary tubes, and isolating separated molecular species from the matrix may be inconvenient in that exhaustive dialysis or electroelution are required.

5. SUMMARY OF THE INVENTION

It is one general object of the invention to provide a supported matrix for use in electric field-induced separation of molecular components, which substantially overcomes or reduces problems and limitations associated with temperature-stabilized or crosslinked polymer matrices of the type described above.

It is yet another object of the invention to provide a method of preparing and using such supported medium.

The invention includes, in one aspect, a method of preparing a supported matrix for use in electric field-induced separation of molecular components in a sample. The method includes first forming an aqueous, viscoelastic polymer matrix characterized by (i) a water-soluble, substantially non-crosslinked polymer, having a molecular weight of at least about 5–10 kilodaltons, and (ii) a viscosity of at least about 5,000 centipoise. This viscoelastic polymer matrix is then pumped into an elongate separation chamber, filling the chamber substantially uniformly with the matrix.

In one embodiment, the separation chamber may be contained within a capillary tube having a plug, such as a glass frit, at one end to prevent flow of the polymer through that tube end, but allowing ions to pass.

The polymer forming the matrix is preferably a linear polymer having a molecular weight of at least about 100,000 daltons. Preferred polymers for separation of proteins are polyethyleneglycol (polyethylene oxide), polyacrylamide, polymethacrylamide. Preferred polymers for the separation of nucleic acid species are polyethylene oxide, polyacrylamide, and hydroxylated polymers, including hydroxylated alkyl cellulose polymers and polyvinyl alcohol.

In another aspect, the invention includes a supported matrix prepared by the above method, for use in electric field-induced separation of molecular components in a sample. The matrix may contain an electrolyte, for electrophoretic separation of sample components, or an ampholyte, for separation of sample components by isoelectric focusing (IEF) in a pH gradient.

Another aspect of the invention is an electrophoretic method for separating components of a sample. In practicing the method, sample is applied to one end of the supported matrix of the type described above, and an electric field is established across the matrix. The type, molecular weight, and concentration of the polymer may be varied to optimize fractionation of a given sample of peptides or nucleic acids. At suitable matrix conditions, it is possible to separate phosphorylated oligonucleotides from their non-phosphorylated analogs.

The method may further include, following electrophoretic separation, removing the matrix containing separated sample components, and isolating separated sample components from the matrix. Isolating the sample from the excised region of the matrix can be carried out conveniently by liquefying the matrix by dilution or removing it by precipitation.

In one preferred embodiment of the electrophoresis method for fractionating nucleic acid species, the polymer matrix is formed from a mixture of polymers. One of the polymers in the mixture, exemplified by polyacrylamide or polyethylene oxide, is effective to fractionate nucleic acid by a sieving mechanism which is dependent on both the size and concentration of the polymer. The other polymer in the mixture, exemplified by a water-soluble, hydroxylated cellulose compound, apparently acts to separate different molecular weight species on the basis of hydrophilic interaction which is dependent on polymer concentration, but not polymer molecular weight.

The invention further includes a method of separating molecular components in a sample by IEF in the above matrix. The matrix used in the method contains an ampholyte effective to form a selected pH gradient within the matrix under the influence of an electric field. Sample components separated in the matrix may be identified and/or isolated by pumping the matrix from the chamber.

These and other objects and features of the invention will become more fully apparent when the following detailed description of the invention is read in conjunction with the accompanying drawings.

DETAILED DESCRIPTION OF THE INVENTION

Figure 1:
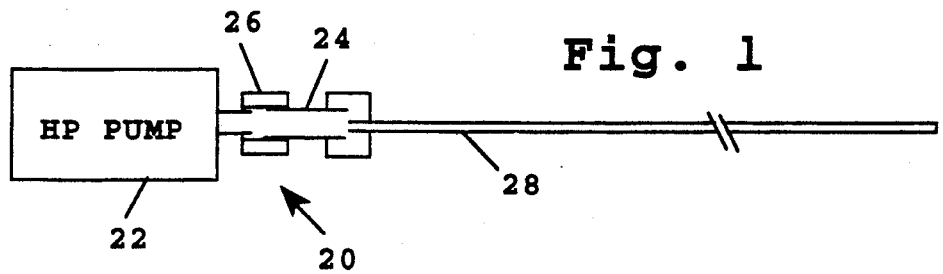
FIG. 1 is a simplified view of a pumping system used for (a) measuring the viscosity of a viscoelastic polymer solution, and (b) filling a capillary tube with such a matrix, in accordance with the invention.

Section I describes the supported polymer matrix of the invention, and methods of preparing and characterizing the polymer solution forming the matrix. Methods of separating biomolecular components, such as proteins and nucleic acids, by electrophoresis in the supported matrix are described in Section II. Isoelectric focusing methods employing the supported matrix are given in Section III.

I. SUPPORTED POLYMER MATRIX

A. Polymers

The polymers used in the preparing the supported matrix of the invention are water-soluble (hydrophilic) polymers which are capable of forming a viscoelastic fluid above a given polymer concentration in an aqueous medium. As defined herein, a "viscoelastic fluid" is one which has a viscosity above about 1,000 centipoise, and may have a viscosity of 400,000 centipoise and greater, and has elastic properties, as evidenced by its tendency, on stretching, to form string-like filament(s) which resist the stretching force. This viscoelastic behavior is similar to the "stringing" which occurs, for example, in rubber cement (which is formed of hydrophobic polymers).

The viscoelastic properties of the polymer are observed generally in linear water-soluble polymers having a molecular weight greater than about 10 kilodaltons (10,000), preferably greater than 100 kilodaltons, and typically between about 0.5 to 10 million daltons. The concentration of polymer needed to achieve the requisite viscoelastic state is dependent on the molecular weight of the polymer, and can range from about 40 weight percent for the smallest polymers, e.g., 10–100 kilodaltons, to 0.1–5 weight percent for polymers greater than 1 million daltons.

This relationship between polymer molecular weight and concentration can be understood from the following simplified picture of polymer interaction. First, the viscoelastic properties of the polymer matrix are due to polymer chain entanglements which allow the material to stretch and exert and counter elastic force, as the intertwined chains are stretched. Secondly, in its ability to form tangled polymer chains, the polymer may be viewed as having opposite end regions which do not contribute to chain entanglements, and a center region which does. Since viscoelastic properties are difficult to achieve below about 5–10 kilodaltons, the size of the opposite end regions which does not contribute to entanglements is assumed to be close to 2–5 kilodaltons, for a linear polymer. At relatively low molecular weight, the portion of the polymer contributes to chain entanglements is relatively small, and thus a high polymer concentration is required, whereas the opposite is true for high molecular weight polymers. Additionally, as the size of the polymer increases, the potential for multiple entanglements increases, reducing the polymer concentration at which viscoelastic properties are observed.

It will be appreciated from the above that high molecular weight branched polymers would be able to form an entangled-chain matrix, but only if the polymer branches are themselves quite long, e.g., corresponding in molecular weight to about 5–10 kilodaltons. Preferred polymers for use in the present invention are linear polyoxides, polyethers, such as polyethylene oxide (polyethyleneglycol), and polypropylene oxide, polyethylene imine, polyacrylic acid, polyacrylamide, polymethacrylamide, polymethacrylic acid, polyvinylacetate, polyvinylpyrrolidone, polyvinyloxazolidone, and a variety of water-soluble hydroxyl polymers, such as natural gums (xanthin, dextran, guar, etc.), water-soluble cellulose compounds, such as methylcellulose and hydroxyethylcellulose, and co-polymers and blends of these polymers.

Suitable water-soluble polymers having a wide range of molecular weights (often expressed in terms of solution viscosity, at a given polymer concentration) are available commercially, or can be prepared under defined polymer formation conditions, as illustrated in the examples below. Example 1A describes matrix formation with polyethylene oxide (PEO), at molecular weights of 900 and 7,000 kilodaltons. Example 1B describes matrix formation with hydroxyethylene cellulose (HEC) having a broad range of viscosities. The matrix described in Example 1C is formed by polymerizing acrylamide monomer in the presence of suitable polymerizing agents to form a linear polyacrylamide matrix.

As will be discussed below, and in accordance with one aspect of the invention, the polymer matrix with desired viscoelastic properties is formed outside a tube support, and subsequently introduced into the tube under high pumping pressure. An important advantage of this approach, over prior art methods in which a polymer material is solidified within a tube support, is the ability to achieve desired matrix properties by controlling reaction conditions, such as temperature, pressure, mixing conditions, light input (for photopolymerized polymers), concentration of polymerizing agents (which may require continued addition of the agents to the reaction mixture), time of reaction termination, ad curing conditions. Further, after polymerization, unwanted reaction products can be removed and/or the polymers can be treated to remove unwanted polymer sizes. In addition, as indicated above, the reaction can be carried out under conditions which avoid inhomogeneities in the matrix due to local heat gradients, bubble formation, poor mixing of reaction components and polymer matrix shrinkage. The polymerization reaction is carried out under conditions in which the polymer remains substantially non-crosslinked.

The polymerization reaction, for use in forming a viscoelastic matrix, is illustrated by the polyacrylamide matrix formed in Example 1C, where polymerization of acrylamide monomer was carried out under controlled reaction conditions until a desired polymer viscosity was achieved.

To form a polymer matrix from prepolymerized material, the polymer may be added, for example, in powder form to a given volume of aqueous medium, and the polymer allowed to disperse under selected mixing conditions, for example with vortexing. Typically, the matrix is allowed to sit for several hours after mixing to insure complete dissolution of the material. If desired, additional aqueous medium may be added to the matrix to reduce viscosity, or the matrix may be dehydrated, for example, under reduced pressure, to increase viscosity. This method is illustrated in Example 1C.

Alternatively, the polymer may be pressed into block or slab form, such as by sintering in a press, and the slab is then cut into a known-weight sections for dissolution in a known volume of aqueous medium. Typically, the polymer block is allowed to dissolve in the medium at room temperature for several hours until the matrix has a uniform consistency. Example 1A illustrates this approach for preparation of different molecular weight PEO matrices.

A polymer matrix prepared for use in electrophoresis (Section II) is formed in an aqueous electrolyte medium, such as a conventional Tris-borate or the like. The electrolyte solution may be formulated to include water-miscible solvents, such as DMSO, ethanol, or the like, if necessary, to increase the solubility of certain molecular species in the matrix. The matrix prepared for use in isoelectric focusing (IEF) is prepared to include standard ampholyte solutions designed to form a selected pH gradient, on equilibration in an electric field.

B. Viscosity Characteristics

The polymer matrix is formed as above to have a viscosity, at room temperature of at least about 5,000 centipoise, and preferably above about 50,000 centipoise.

For polymer solution viscosities less than about 250,000 centipoise, solution viscosity can be measured using a conventional viscometer. In operation, a viscometer rotates a spindle immersed in the test liquid through a spring. The degree to which the spring is wound, detected by a rotational sensor, is proportional to the viscosity of the fluid. Table 1 below shows viscosity values measured for high molecular weight polyacrylamide (PA) at the various polymer concentrations indicated. The polymers were prepared substantially as described in Example 1C.

The viscosity of the polymer matrices was measured using a Brookfield Digital Viscometer Model #DV-11 (Stoughton, MA). A #27 spindle was used in combination with the Brookfield small sample adaptor. The viscosities were measured at 25° C, and are expressed in centipoise.

TABLE 1

| Polymer | Conc. | Viscosity | Spindle RPM |
|---------|-------|-----------|-------------|
| PA | 3.0 | 210 | 50 |
| PA | 4.5 | 388 | 50 |
| PA | 6.0 | 7,250 | 1 |
| PA | 7.5 | 35,500 | 1 |
| PA | 9.0 | 161,000 | 1 |
| PA | 10.5 | 204,000 | 1 |
| PA | 12.0 | 404,000 | 1 |

At high polymer viscosities, where the fluid has a grease-like consistency, the rotating spindle of the viscometer produces a cavity within the fluid, preventing reliable viscosity measurements. At high viscosities in which the fluid has a highly elastic character, the fluid tends to wrap itself, stringlike, about the spindle, also preventing accurate viscosity measurements. With either type of high-viscosity fluid, it is necessary to measure viscosity by alternative means.

One system for performing viscosities measurements of highly viscous, elastic polymer solution is illustrated at 20 in FIG. 1. The system includes a high pressure pump 22 of the type used for high-pressure liquid chromatography. One suitable pump is a Model 140A high-pressure pump available from Applied Biosystems (Foster City, CA). The pump is connected to a stainless steel tube 24 which is connected to the pump through a fitting 26, such as connector Part #U437 available from Upchurch Scientific Inc. (Seattle, WA).

The distal end of the tube is connected to a capillary tube 28, also through a high pressure fitting of the type described above. The capillary tube has a preferred lumen diameter of between 50 and 100 microns, and a preferred length of between about 20–40 cm.

To perform a viscosity measurement, the steel tube is filled with the polymer matrix, typically using a syringe, to force the matrix material into tube 24. With activation of the pump, at a selected pumping volume rate, the pump pressure will increase until the preset pumping rate is achieved, up to a maximum pump pressure, e.g., 5,000 psi, at which point the pump maintains the upper-limit pressure. The viscosity is then measured as (a) the pump pressure when the matrix material has been pumped through the entire length of the capillary tube, or (b) at higher viscosities, the distance the matrix material has traveled when the pump reaches its maximum pressure.

In the following viscosity measurements, a clean 30 cm of 75 μm capillary was attached to the high pressure pump for each of viscosity determination. The flow rate was set at 100 microliters per minute on the pump and the polymer matrix was loaded as just described. The pump pressure or travel times are given in the Table 2 below.

TABLE 2

| Polymer Type | Conc. | Pressure To Reach End | Distance Traveled |
|---|---|---|---|
| PEO/WSR 1105 | 11.2 | 5000+ | 19 cm |
| PEO/WSR 303 | 11.2 | 5000+ | 20 cm |
| PEO/WSR 303 | 6.0 | 3000 | 30 cm |
| PA | 3.0 | 543 | 30 cm |
| PA | 4.5 | 892 | 30 cm |
| PA | 6.0 | 1334 | 30 cm |
| PA | 10.0 | 3018 | 30 cm |
| HEC/3L | 10.0 | 5000+ | 29 cm |
| HEC/40 | 10.0 | 5000+ | 25 cm |
| HEC/300 | 10.0 | 5000+ | 21 cm |
| HEC/4440 | 10.0 | 5000+ | 5 cm |
| Water | — | 90 | 30 cm |

Figure 2:
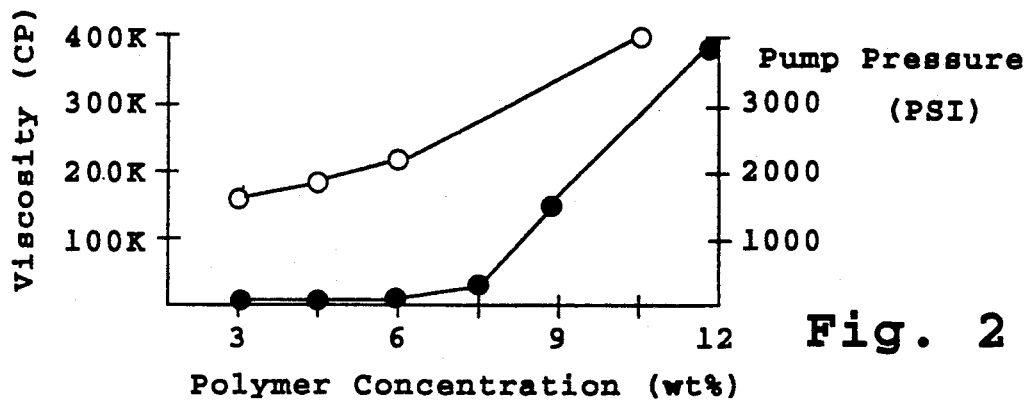
FIG. 2 is a plot of polymer viscosity, as measured by a viscometer (left ordinate, closed circles) or by flow characteristics through a capillary tube (right ordinate, open circles) plotted as a function of polymer concentration.

A plot of viscosity as a function of polymer concentration is given in FIG. 2, showing the change in viscosity measured by a Brookfield viscometer (solid circles) and as measured by flow pressure (open circles) for various concentrations of polyacrylamide.

As seen from the plot, the viscosity curve has a bend or elbow at about 6% polyacrylamide, corresponding to a polymer viscosity of about 7,000 centipoise and a pumping-pressure viscosity of about 1300 psi, under the above pumping conditions. Experiments aimed at determining the lowest polymer concentration effective to resolve proteins by electrophoresis demonstrate that resolution of proteins in the 14-30 kilodalton size range is lost significantly below about 5-6% PA, corresponding to a viscosity of about 5,000 centipoise.

The viscosity of the matrix which is used in practicing the invention will be dictated by a number of factors whose importance will be described in Sections II and III below. As noted above, a minimum viscosity of about 5,000 centipoise is required for protein fractionation by capillary electrophoresis and this value defines the lower limit of viscosity in a viscoelastic polymer solution useful in the present invention.

For use in electrophoretic separation of molecular components in which fractionation is based on a polymer sieving effect (Section II), lower solution viscosities, such as between 5,000 to 100,000 centipoise, are suitable for resolving relatively high molecular weight components, such as proteins in the 20-50 kilodalton and higher range. For smaller peptides, polymer viscosities of about 2,000-3,000 psi or greater are suitable. For nucleic acid fractionation by electrophoresis, the viscosity of the medium may vary widely for hydroxylated polymers, which appear to effect fractionation by a non-sieving interaction with nucleic acid species, as will be described in Section II.

The viscosity of the solution may also be dictated by desired physical characteristics of the supported matrix. Thus, where it is desired to process the matrix in an intact form 1 after separation, the viscosity of the matrix must be sufficient to allow expulsion of the matrix under pressure in intact form.

C. Supported Matrix

The supported matrix of the invention includes a support, typically a capillary or preparative-scale tube, defining an elongate separation chamber, and a polymer matrix of the type described above which fills the chamber uniformly and homogeneously, as described below.

FIG. 2 shows an enlarged fragmentary portion of a capillary-tube supported matrix 30 formed in accordance with the invention. The capillary tube support 2 is a conventional capillary tube, typically having a length between about 10-200 cm, typically less than about 100 cm, and an inner diameter of preferably between about 25-200 μ (microns), typically about 50 μ.

Where the tube is a fused silica capillary, the inner wall has negative silane groups which may produce electroosmotic flow effects, as described, for example, in co-owned U.S. patent application for "Nucleic Acid Fractionation by Counter-Migration Capillary Electrophoresis", Ser. No. 390,631, filed Aug. 7, 1989. If desired, electroosmotic flow in a charged-wall capillary can be substantially eliminated by one of four approaches. In the first approach, the viscosity of the polymer is made sufficiently high, e.g., at a pumping pressure flow rate of 3,000-5,000 psi, that little or no electroosmotic flow can occur during the period of electrophoresis.

Figure 3:
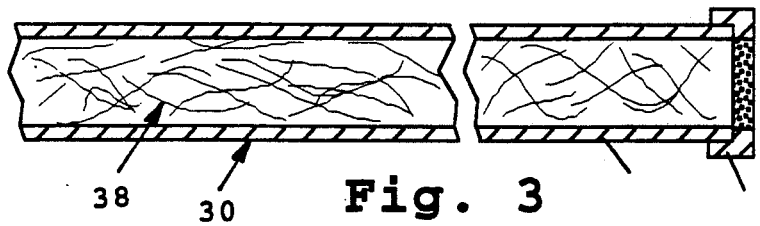
FIG. 3 is an enlarged, fragmentary portion of a capillary-tube supported matrix constructed according to the invention.

In a second approach, the capillary tube is provided with a water-permeable plug, such as plug 36 seen in FIG. 3, or other obstruction which substantially prevents flow of a viscoelastic matrix out of the tube.

Another approach is based on chemical bonding of the matrix, after injection into the tube, with the walls of the tube. Here the tube is first chemically treated with a bifunctional coupling agent capable of reacting with chemical groups on the tube wall and with the polymer in the matrix. Silane coupling agents are suitable, for example, for fused silica tubes, and examples of silane bifunctional reagent chemistry can be found in "Silane Coupling Agents", Plenum Press, NY, 1982.

Finally, the electrophoresis tube may have coated walls, such as Teflon-coated walls, to mask surface wall charges or the tube itself may be formed from non-charged polymer material such as Teflon.

Preparative-scale electrophoresis tubes in a variety of tube diameter and length sizes are available for use as a support in the invention. Typically, tube diameters of about 1-10 mm, and tube lengths of between about 3-20 cm are employed for preparative scale fractionation. Flow of matrix material in the tube may be prevented, as above, by the use of a frit or constricted plug or the like which prevents flow of the viscoelastic material out of the tube, but allow ion migration across the tube end. Alternatively, or in addition, at high viscosities in the range 3,000 or greater pumping pressure, the matrix may be relatively stable against flow under gravity during the period of electrophoresis.

The tube support—either capillary or preparative-scale tube—defines an elongate separation chamber, indicated at 38 in FIG. 3, which may include the entire length of the tube lumen or only a portion thereof. For example, it may be desired to fill one end region of the tube with a buffer solution. The matrix support is prepared, in accordance with the invention, by pumping the polymer matrix into the separation chamber, to fill the chamber substantially uniformly with the matrix.

The pumping system shown in FIG. 1 is generally suitable for pumping polymer matrix into a capillary or preparative-scale tube. As above, the system is loaded with the polymer solution, and the pump is set to a selected pumping speed typically 50–1,000 µl min. The material is pumped into the tube until the separation chamber (which may include only a portion of the tube) is filled.

When pumped into the tube, the matrix material fills the chamber substantially uniformly and homogeneously, by which is meant the polymer matrix in the chamber has a substantially uniform density throughout the chamber, with substantially no discontinuities or voids in the matrix. This feature is achieved by virtue of (a) the uniform density and homogeneous bulk properties of the matrix which are achievable by forming the matrix outside of the tube, (b) the ability to pump the matrix into the tube without breaks, cracks, or voids forming in the matrix, and (c) the ability of the matrix to completely fill the chamber space as it is pumped into the tube.

The advantages of the supported matrix, as a medium for electrophoretic separation, can be appreciated from the foregoing. The matrix can be formed to a high viscosity, by a combination of high polymer molecular weight and/or concentration, for fractionating closely related molecular species, particularly small peptides and oligonucleotides. At the same time, the resolution achievable in the medium is significantly improved over prior art high-concentration gel-electrophoresis methods, by virtue of the greater homogeneity and lack of voids in the medium.

II. ELECTROPHORESIS METHOD

A. Capillary Electrophoresis System

Figure 4:
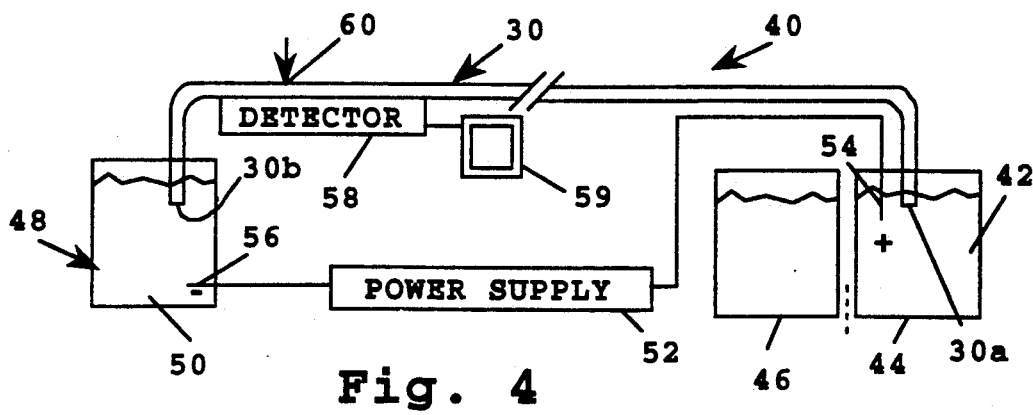
FIG. 4 is a schematic diagram of a capillary tube system used in practicing electrophoresis or IEF methods, in accordance with the invention.

FIG. 4 is a simplified schematic view of a capillary electrophoresis system 40 suitable for practicing the method of the invention. The system includes a capillary-tube supported matrix 30, such as described above with reference to FIG. 3.

An anodic reservoir 42 in the system contains an electrolytic solution 44. The anodic end of the tube, indicated at 30a, is immersed in the solution, as shown, during electro-phoresis. A reservoir 46 in the system may contain a marker solution, or may contain a sample of (positively charged) molecules to be separated, during an electrophoretic separation. Preferably the marker or sample material is dissolved in the electrolytic solution or in water. The two anodic reservoirs may be carried on a carousel or the like, for placement at a position in which the lower anodic end of the tube can be immersed in the reservoir fluid.

The opposite, cathodic end of the tube, indicated at 30b, is sealed within a cathodic reservoir 48 and is immersed in an cathodic electrolyte solution 50 contained in the reservoir, as shown.

A high voltage supply 52 in the system is connected to the anodic and cathodic reservoirs as shown, for applying a selected electric potential between the two reservoirs. The power supply leads are connected to platinum electrodes 54, 56 in the anodic and cathodic reservoirs, respectively. The power supply may be designed for applying a constant voltage (DC) across the electrodes, preferably at a voltage setting of between 5–50 KV Alternatively, or in addition, the power supply may be designed to apply a selected-frequency, pulsed voltage between the reservoirs. In general, the shorter the capillary tube, the higher the electric field strength that can be applied, and the more rapid the electrophoretic separation. The polarity of the electrodes is, of course, reversed for separating negatively charged species.

Completing the description of the system shown in FIG. 1, a detector 58 in the system is positioned adjacent the cathodic end of the tube, for optically monitoring nucleic acid fragments migrating through an optical detection zone 60 in the tube. The detector may be designed either for UV absorption detection and/or for fluorescence emission detection UV absorbance is typically carried out at 200–280 nm, using, for example, a Kratos 783 UV absorbance detector which has been modified by Applied Biosystems (Foster City, CA.), by replacing the flow cell with a capillary holder. Fluorescence emission detection is preferably carried out at a selected excitation wavelength which is adjustable between about 240–500 nm, depending on the fluorescent species associated with the nucleic acid fragments, as discussed below. One exemplary fluorescence detector is an HP1046A detector available from Hewlett-Packard (Palo Alto, CA), and modified as above for capillary tube detection. The detector is connected to an integrator/plotter 59 for recording electrophoretic peaks.

B. Detection and Isolation Methods

Figure 5:
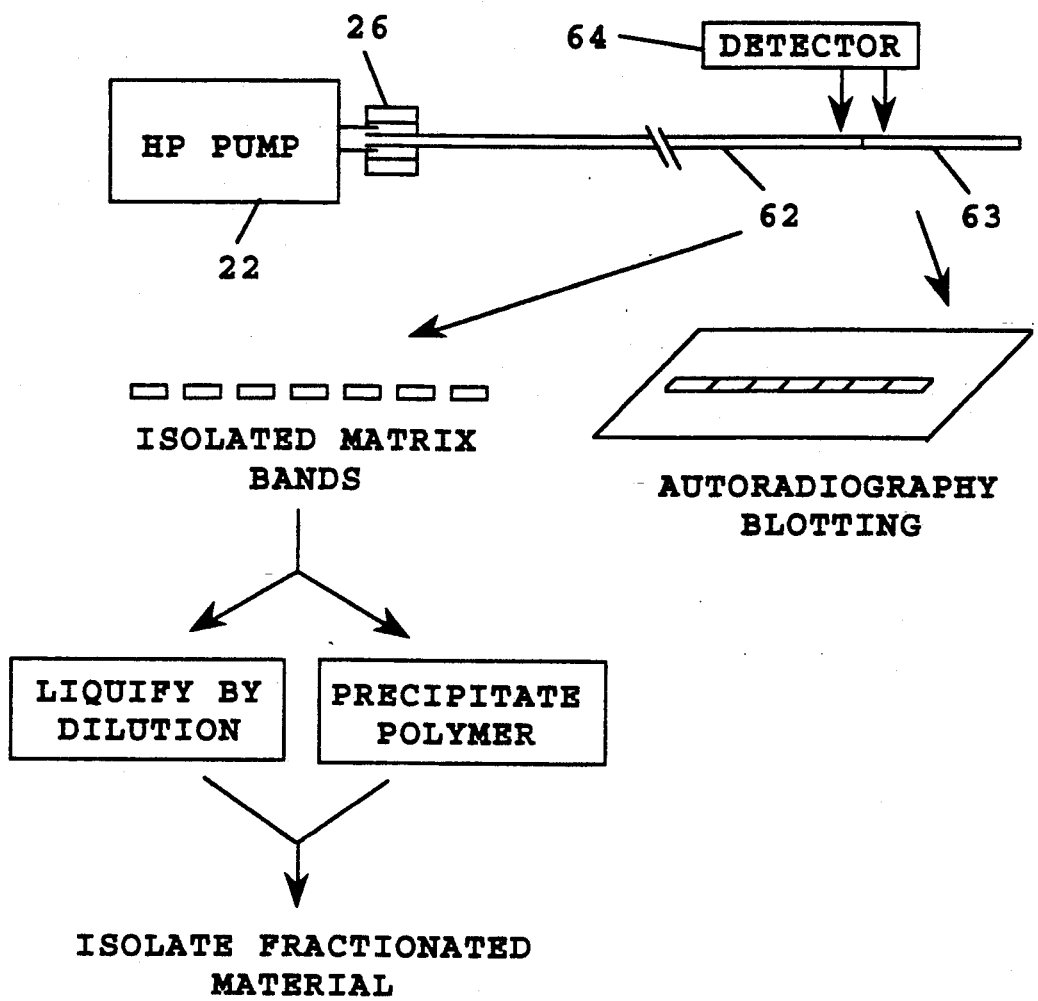
FIG. 5 is a schematic view of steps which may be employed for detecting and isolated fractionated species in a viscoelastic matrix, in accordance with the invention.

FIG. 5 illustrates a variety of methods which may be employed to detect and/or isolate fractionated molecular species after electrophoretic separation. The methods are applicable particularly to a capillary-tube matrix, although a preparative-scale matrix may be required, particularly for isolation of protein and peptide species.

One standard detection system, discussed above, employs a detector for detecting migration of molecular species through a detection zone located within downstream end region of the gel, as the species migrate out of the matrix.

Alternatively, where it is desired to detect species in the matrix or isolate species from the matrix, the electrophoretic run is stopped before the fastest migrating species of interest reaches the downstream end of the matrix. The tube, here indicated at 62, is then connected to a high-pressure pump 22, through a fitting 26, as described above, and the pump is set at a pumping rate suitable for expulsion of the matrix in intact form, such as 50–1,00 µl minute for a capillary tube matrix.

According to an important advantage of the invention, the fluid character of the matrix allows it to be expelled from the tube—either capillary or preparative-scale tube—in intact form. For this purpose, a polymer matrix with a viscosity of greater than 2,000–5,000 psi, as defined above, is preferred, in order to provide sufficient cohesiveness and form to the matrix as it is pumped from the tube.

As the matrix, indicated at 63, is being expelled from the tube, the fractionated species in the matrix can be monitored by a detector 64 whose detection zone is placed either upstream or downstream of the tube, as indicated. As above, the detector can be employed in generating an electropherogram which can be used to identify selected bands in the matrix, after expulsion from the tube, with known distances along the length of the gel. Alternatively, the matrix can be removed in intact form can "read" in a conventional gel scanner to generate an electropherogram of fractionated molecular species.

To isolate fractionated species of interest, typically the electropherogram is divided into short sections, as indicated in FIG. 5, and those sections corresponding to bands of interest are further processed to obtain the desired isolated species. Two convenient methods are available for isolating separated molecules from the matrix. In the first, shown at the lower left in FIG. 5, the matrix is diluted with an aqueous medium, to produce a low-viscosity protein solution which can then be further processed, for example, by column chromatography or addition of a precipitating agent, to isolated the desired molecular species, or by addition of Polymerase Chain Reaction (PCR) reagents, to amplify nucleic acid species in the dissolved matrix. Alternatively, the polymer forming the gel can be precipitated, such as by acid precipitation, and filtered to obtain released molecular species.

The lower right portion of FIG. 5 illustrates band detection by autoradiography, where the fractionated species are radiolabeled. Here the intact matrix expelled from the tube is placed on sensitive film, and after a sufficient exposure time, developed according to standard autoradiography methods to reveal the positions of the fractionated, labeled species.

Alternatively, the molecular species can be transferee to a suitable filter disc or the like by (a) placing the matrix on the disc, (b) applying a vacuum to the disc, while heating the matrix to allow it to be drawn through the filter, and (c) collecting the fractionated material on the disc. The species trapped on the disk may be prelabeled, or identified by reaction with a suitable radiolabeled, species-specific probe, such as a labeled antibody or DNA probe. This technique can be employed, for example, as a modified Western-blot technique for transferring fractionated nucleic acid species onto a nitrocellulose filter, and identifying bands of interest by their hydribization with a sequence-specific probe.

D. Protein Fractionation

The electrophoretic method of the invention may be employed for fractionating peptides and proteins over a wide size range, from small peptides to proteins of molecular weight up to 100,000 daltons or greater. Experiments carried out in support of the invention indicate that electrophoretic separation of proteins is based on a sieving effect in which the molecules are retarded, in passing through the matrix, by the polymer mesh forming the matrix, with larger polypeptides migrating more slowly through the matrix than smaller peptides (with a similar charge density) in an electric field.

Figure 6A:
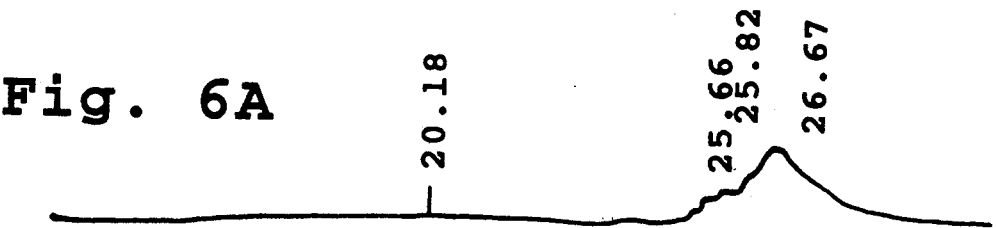
FIGS. 6A are electropherograms of proteins fractionated on a matrix prepared with 4.5 weight percent (6A), 7.5 weight percent (6B), and 10 weight percent polyacrylamide(6C)
Figure 6B:
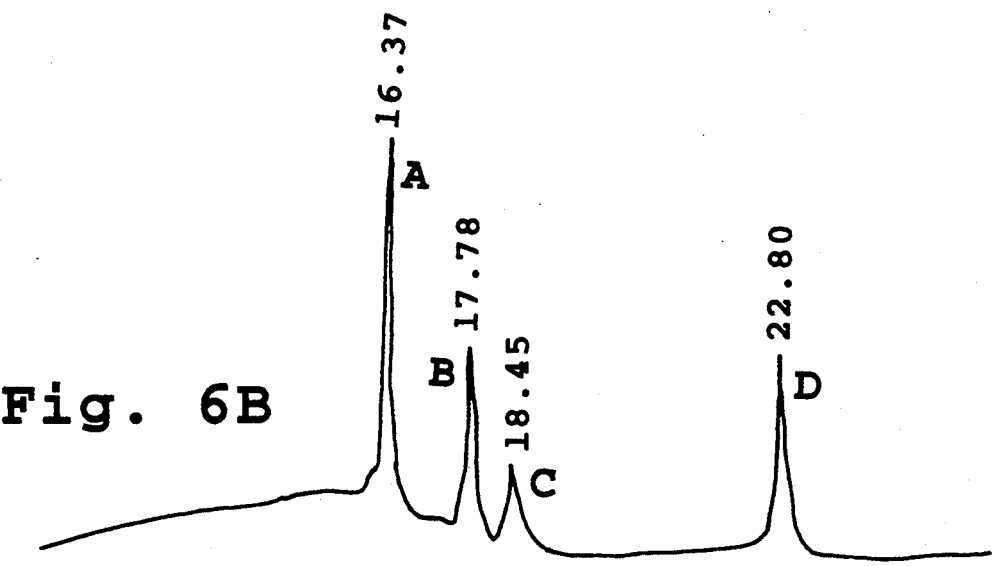
Figure 6C:
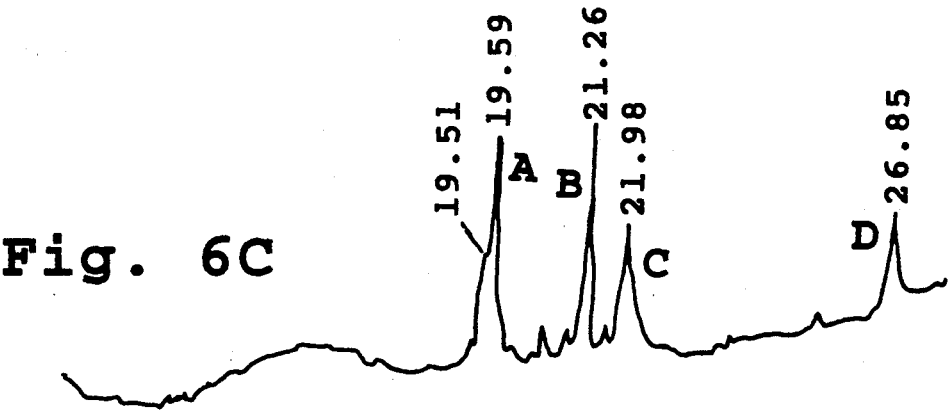

FIGS. 6A–6C show electrophoretic separation of proteins in the 14.2 to 29 kilodalton range, as described in Example 2. The FIG. 6A separation was performed at 4.5 weight percent polyacrylamide, prepared as in Example 1C. The viscosity of the medium was about 338 centipoise, and the matrix at this viscosity is clearly unable to effect protein separation. The same proteins fractionated in 7.5 weight percent polyacrylamide, corresponding to a viscosity of about 35,000 is shown in FIG. 6B, showing good separation of the four protein species. Even greater resolution was achieved at a 10 weight percent polyacrylamide concentration (FIG. 6C), corresponding to a viscosity of greater than 200,000 centipoise.

Thus, for proteins in the size range between about 10 and 30 kilodaltons, a matrix viscosity between about 35,000 200,000 centipoise is suitable. For larger molecular weight protein, viscosities in the range 5,000 to 100,000 are preferred. Conversely, for low molecular weight peptide, matrix viscosities corresponding to a pumping pressure of 3,000–5,000 psi provide optimal resolution. At the highest viscosities, the method can provide enhanced resolution of small peptide species, such as N- or C-terminal fragments and derivatized analogs thereof.

The desired separation viscosities may be achieved by a combination of polymer molecular weight and polymer concentration, as described above. Specifically, the viscosity and degree of resolution of small species are increased with either higher molecular weight polymer or higher concentration of the polymer. Preferred polymers for polypeptide fractionation are polyacrylamide, polymethacrylamide, and polyalkyl ethers, such as PEO, at polymer molecular weights of at least about 100,000, although a variety of other polymers may be employed.

Electrophoresis is carried out in a conventional electrophoresis system, such as the capillary tube system described with respect to FIG. 4. The polypeptide sample is typically introduced by drawing the same into one end of the tube protein electrophoretically, typically for a period of several seconds, immersing the sample end of the tube in an electrophoresis buffer during electrophoretic separation. The migration of the protein bands past a detection zone near the downstream end of the tube can be monitored spectrophotometrically, as described above. Alternatively, the fractionated proteins can be detected in and/or isolated from the intact matrix, after removal from the tube support, also as described above.

E. Nucleic Acid Fractionation

Studies conducted in support of the present invention indicate a number of unique features of the present invention for electrophoretic separation of nucleic acid species.

One feature of the invention is the discovery that nucleic acids may be separated on high-viscosity polymer matrices by either of two distinct separation mechanisms. One separation mechanism involves molecular sieving, similar to the mechanism described above for protein fractionation, and appears to predominate in a matrix whose polymer does not include hydroxyl groups. Exemplary polymers which are effective in sieving-type separation are linear polyoxides, polyethers, such as polyethylene oxide (polyethyleneglycol), and polypropylene oxide, polyethylene imine, polyacrylic acid, polyacrylamide, polymethacrylamide, polymethacrylic acid, polyvinylacetate, polyvinylpyrrolidone, and polyvinyloxazolidone, with polyacrylamide, polymethacrylamide and PEO polymers being preferred.

As discussed in the section above, a sieving mechanism produces greater resolution of small molecular weight species as either the molecular weight of the polymer or polymer concentration is increased, since both variables increase the density of the polymer entanglements in the matrix.

Figure 7A:
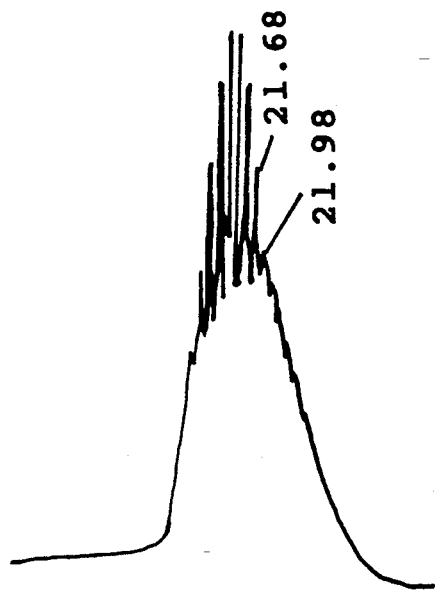
FIGS. 7A and 7B are electropherograms of a 40mer to 60mer oligonucleotide acid ladder fractionated by electrophoresis on linear polyethylene oxide polymers of approximate molecular weight 900 kilodaltons (6A) and 7,000 kilodaltons (6B), both at 11.2 weight percent polymer.
Figure 7B:
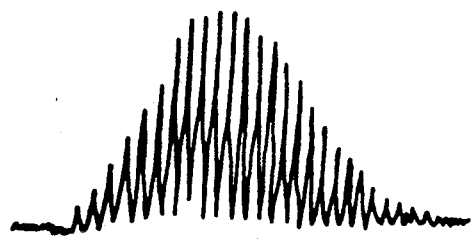

FIGS. 7A and 7B show the resolution of a ladder of single-strand 40mer to 60mer oligonucleotides (40 to 60 bases) in 7.5 weight percent PEO matrices formed with a 900 and 7,000 kilodalton PEO polymers, respectively. Electrophoretic conditions are given in Example 3A. As seen, the oligonucleotides are poorly resolved on the lower molecular polymer matrix, but separated with substantially baseline resolution on the higher molecular-weight polymer matrix.

Figure 8A:
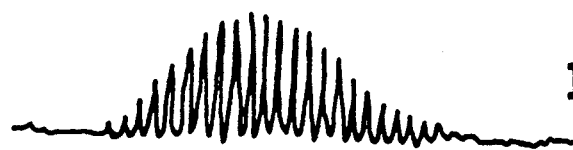
FIGS. 8A and 8B are electropherograms of a 40mer to 60mer oligonucleotide acid ladder fractionated by electrophoresis on a linear polyethylene oxide polymer of approximate molecular weight 7,000 kilodaltons at 6 weight percent (8A) and 15 weight percent (8B)
Figure 8B:
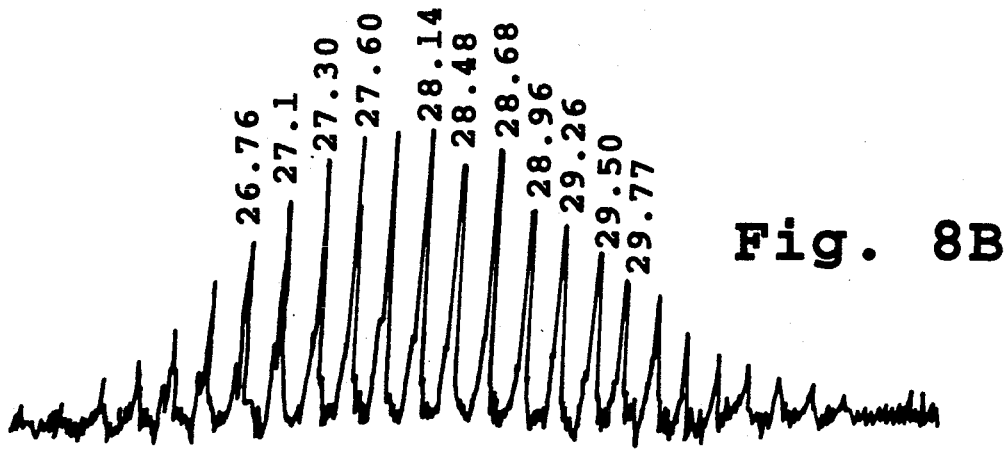

FIGS. 8A and 8B shows the resolution of the same single-strand ladder on 7,000 kilodalton molecular weight polymer at 6 and 15 weight percent polymer, respectively, at the electrophoretic conditions given in Example 3B. As seen, the oligo-nucleotide peaks were much better resolved at the higher polymer concentration.

A second, distinct separation mechanism is observed for nucleic acids separated on a matrix formed of a hydroxylated polymer. This mechanism appears to involve an interaction of the nucleic acid with polymer hydroxyl groups, rather than a sieving effect, and has been observed in a variety of hydroxylated polymers, such as water-soluble hydroxylated cellulose compounds, as exemplified by hydroxyethylcellulose (HEC) and polyvinyl alcohol. Other suitable hydroxylated polymers include natural gums, such as xanthin, dextran, and guar.

An interaction mechanism would predict that separation of nucleic acid species would be dependent on polymer concentration, since a higher polymer concentration would provide a greater number of nucleic acid/polymer interactions, but should be independent of polymer molecular weight, since this variable would effect the density of polymer entanglement, but not the density of polymer hydroxyl groups.

Figure 9A:
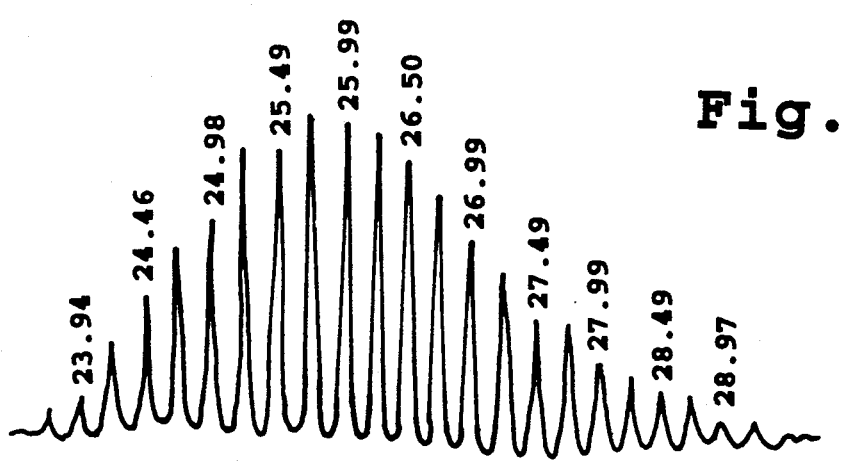
FIGS. 9A–9C are electropherograms of a 40mer to 60mer nucleic acid ladder fractionated by electrophoresis on matrices formed of linear hydroxyethyl cellulose (HEC) polymers having relatively low (9A), intermediate (9B), and high (9C) molecular weights, each at a polymer concentration of about 10 weight percent.
Figure 9B:
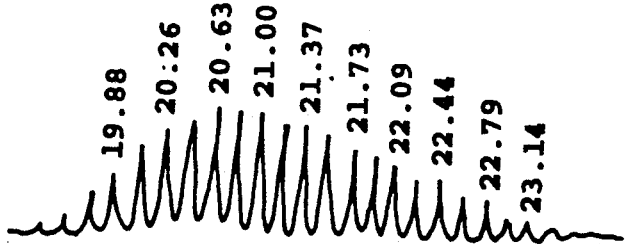
Figure 9C:
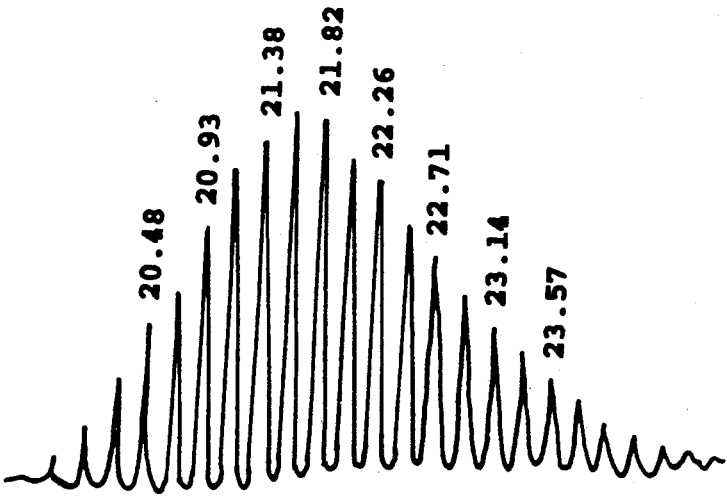

FIGS. 9A through 9C are electropherograms of a ladder of single-strand 40mer to 60mer oligonucleotides in 10 weight percent HEC prepared from low-, intermediate-, and high-viscosity polymers, respectively. As seen, there is no appreciable effect of polymer molecular weight on oligonucleotide resolution. Electrophoretic conditions are described in Example 4A.

Figure 10A:
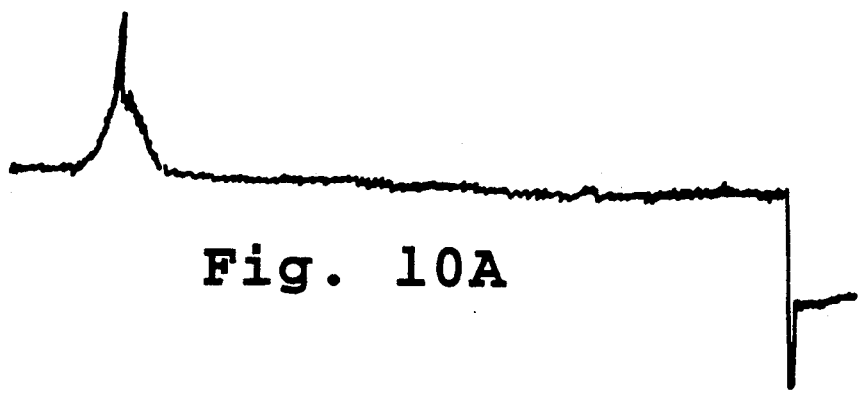
FIGS. 10A–10D are electropherograms of a 20mer to 40mer nucleic acid ladder fractionated by electrophoresis on matrices formed of a linear hydroxyethyl cellulose (HEC) polymer, at polymer concentrations of 3% (10A), 10% (10B), 15% (10C), and 25% (10d)
Figure 10B:
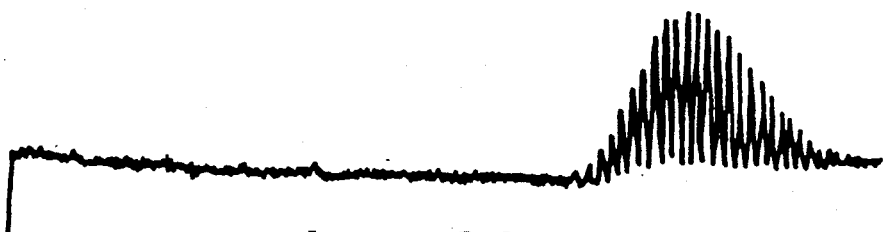
Figure 10C:

By contrast, when the intermediate-viscosity HEC polymer is formulated at increasing concentrations, as detailed in Example in Example 4B, a dramatic increase in oligonucleotide resolution is obtained. This is seen in FIGS. 10A through 10B, which show electropherograms of a 20mer to 40mer single strand nucleotide ladder at HEC weight percent concentrations of 3 (10A), 10 (10B), 15 (10C), and 25 (10D). The spreading of the peaks with increasing polymer concentration is evident.

Figure 11:
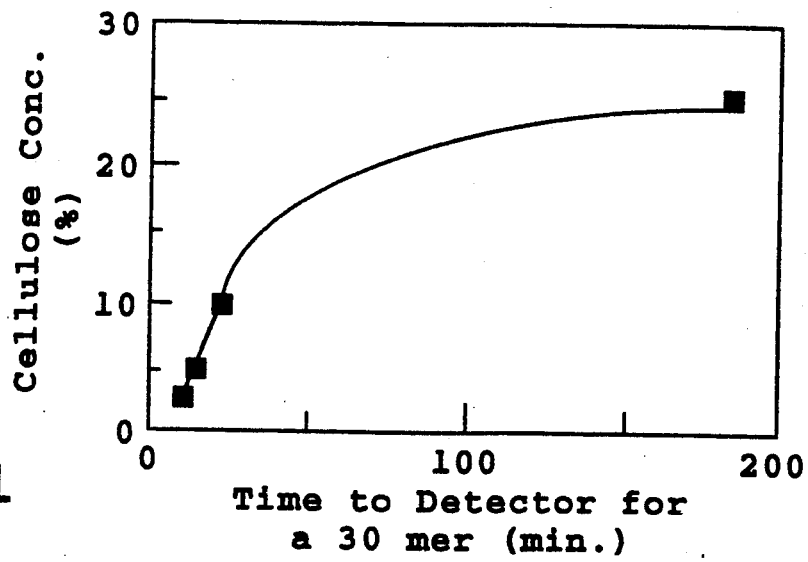
FIG. 11 is a plot of migration rate of a 30mer oligonucleotide, as a function of HEC concentration, derived from the plots in FIGS. 10A–10D.

When time of travel through the matrix of the intermediate 30 mer peak is plotted as a function of polymer concentration in the above studies, the plot shown in FIG. 11 is obtained, demonstrating the greater polymer concentration is associated with slower migration rate through the matrix.

According to another feature of the method, it has been discovered that electrophoretic separation of low molecular weight nucleic acids is enhanced by a combination of sieving and interaction effects in the matrix. Here the method is carried out in a polymer mixture containing at least one non-hydroxyl polymer, such as polyacrylamide or PEO, for sieving, and at least one hydroxylated polymer, such as a water-soluble hydroxylated cellulose compound, capable of a non-sieving interaction with the nucleic acid species.

Figure 10D:
Figure 12:
FIG. 12 is electropherogram of a 40mer–60mer nucleic acid ladder fractionated by electrophoresis on matrices formed of a linear hydroxyethyl cellulose (HEC) polymer, at polymer concentrations of about 5.5 weight percent, and polyacrylamide, at a concentration of about 11 weight percent.

The mixed-polymer matrix method is illustrated in Example 6, for fractionation of a 40mer to 60mer single strand oligonucleotide ladder. The matrix is prepared from a polymer mixture containing about 11 weight percent polyacrylamide, as the "sieving" polymer, and about 5.5 weight percent HEC as the "interacting" polymer. The electropherogram of the fractionated oligonucleotides as shown in FIG. 12. As seen, the peaks are resolved to an extent seen only in an HEC matrix at 25 weight percent (FIG. 10D). A comparison of the resolution achievable in a 10 weight percent sieving polymer (FIG. 8A) and 5 weight percent "interaction" polymer (FIGS. 10A, 10B) indicate that the combination of the two polymer types provides significantly better resolution than what would be expected from either polymer alone.

A third feature of the invention, as it applies to electrophoresis of nucleic acids, is the ability to resolve oligonucleotide analogs, and in particular, phosphorylated and non-phosphorylated oligonucleotide analogs. The method is illustrated in Example 5, which describes electrophoretic separations of a ladder of single-strand 12mer to 18mer oligonucleotides, resolved on a matrix support formed of 10 weight percent HEC.

Figures 13A, 13B:
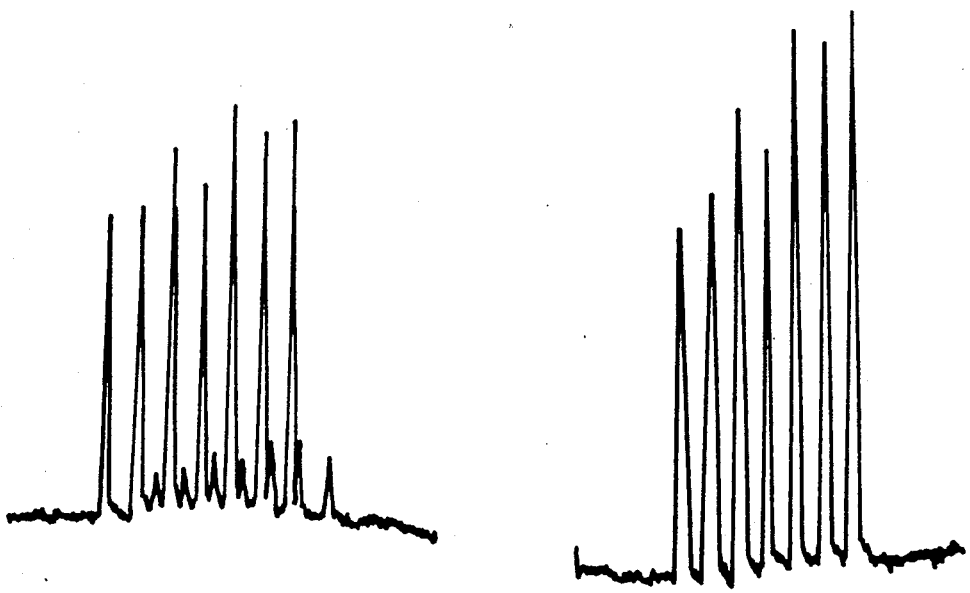
FIGS. 13A–13C are electropherogram of sets of polyadenylic acid including both phosphorylated (dominant species) and non-phosphorylated (minor) species (13A), non-phosphorylated species only (13B), and a mixture of phosphorylated and non-phosphorylated species (13C) fractionated by capillary electrophoresis in 10 weight percent HEC.
Figure 13C:
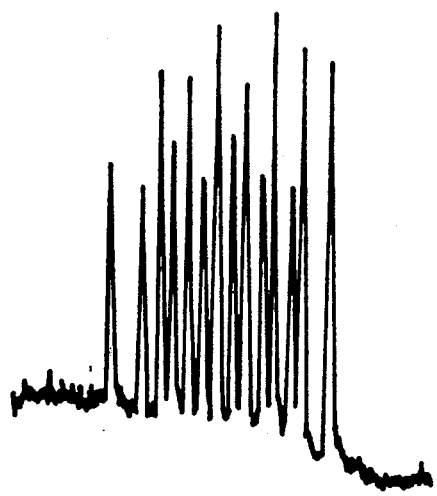

FIG. 13A is an electropherogram of the phosphorylated oligomer ladder, showing the baseline resolution of the seven major oligomer peaks. Also seen in the electropherogram are seven minor peaks which are "offset" from the major peaks by migration distance corresponding to about 1.5 nucleotide units. An electropherogram of the non-phosphorylated oligomers is seen in FIG. 13B, showing seven clearly resolved peaks. When a mixture of phosphorylated and non-phosphorylated ladders are mixed, the electropherogram seen in FIG. 13C is obtained. A comparison of the three figures indicates that the two fastest moving peaks (at the left) are the phosphorylated 12mer and 13mer. Thereafter the non-phosphorylated and phosphorylated peaks alternate, with the two slowest peaks (at the right) being the non-phosphorylated 17mer and 18mer.

The results demonstrate the ability of the electrophoresis method to separate phosphorylated oligomers from their non-phosphorylated analogs.

III. ISOELECTRIC FOCUSING METHOD

The polymer matrix of the invention is also useful for capillary or preparative-tube IEF, by providing a stable matrix which can be expelled in intact form from the tube after separation of sample components on the pH gradient. Both electrophoresis and IEF are referred to herein as electric field-induced separation of molecular components.

The supported matrix used in carrying out the IEF method is prepared according to the general guidelines above, substituting a standard IEF ampholyte solution for the electrolyte solution used in an electrophoresis matrix. Ampholyte solutions for producing a range of pH gradients, on equilibration in an electric field, are well known.

The type, molecular weight, and concentration of polymer are less critical than in electrophoretic separation, since the polymer matrix does not function as a separation medium. Rather, the polymer composition is selected to (a) minimize band spreading after the electric field is removed, and (b) to facilitate removal of the matrix from the tube after equilibrium is reached. Typically these objective are met in a relatively high matrix viscosities. However, for separation of high molecular weight proteins and nucleic acids, the viscosity must be kept low enough to allow free migration of the molecular species in the gel.

The electrophoresis system like the one illustrated in FIG. 4 is suitable for use in IEF on a capillary-tube supported matrix. Sample loading, voltage settings, and run times are carried out conventionally. Typically the sample contains proteins or peptides which are readily separable, on the basis of different isoelectric points, on the selected pH gradient. After equilibrium is reached, the tube may be removed from the system and scanned. Alternatively, and according to an important advantage of the method, the matrix can be expelled in intact form from the tube, for analysis of separated bands in the matrix by one of the methods described with reference to FIG. 5.

The method enhances the resolution of bands which can be achieved by IEF, since band spreading and wall distortion effects which smear separated bands when a low-viscosity medium is drawn from the tube are eliminated. At the same time, the matrix provides the advantages of a low-viscosity medium in that the pH gradient can be expelled from the tube readily for analysis of the separated molecular components. The expelled matrix also allows for analysis by autoradiography or blotting techniques, as described with reference to FIG. 5.

The following examples illustrate methods of preparing supported matrices, and methods of fractionating proteins and nucleic acids, in accordance with the invention. The examples are intended to illustrate, but in no way limit, the scope of the invention.

EXAMPLE 1

Preparation of Capillary-Tube Matrices

A. Polyethylene Oxide Matrix

High molecular weight linear polyethylene oxide (PEO) was dissolved into viscoelastic gels by the following technique. Two grades of PEO powder were obtained from Union Carbide Corporation (Danbury, CT), WSR-1105 (MW=900,000) and WSR 303 (MW=7,000,000). These powders were sintered into 2.0×0.1 cm slabs in a press. The slabs were then weighed and placed into a volume of Tris-Borate buffer containing 10 mM Tris-borate, pH 8.3, 5 mM NaCl, and 0.1 mM EDTA, (TB buffer), in an amount sufficient to produce a final polymer concentration of 11.2 weight percent. The buffer solution was obtained from Sigma Chemical (St. Louis, MO).

The polymer solution was allowed to come to equilibrium for 24 hours. The lower molecular weight polymer (WSR1150) formed a polymer matrix with a greaselike consistency, and a the higher molecular weight polymer formed a matrix with a soft elastic gel.

B. Hydroxethyl Cellulose Matrix

High molecular weight linear hydroxyethyl cellulose was obtained from Union Carbide Corporation (Danbury, CT). Five grades were used in studies on the effect of polymer molecular weight. The molecular weights are quantified by solution viscosity by Union Carbide Corporation and are listed below

| Grade | Viscosity Range | Spindle No. | RPM |
|---|---|---|---|
| QP3L | 215–282 | 1 | 30 |
| QP300 | 300–400 | 2 | 60 |
| 40 | 300–500 | 1 | 30 |
| QP4400 | 4,800–6,000 | 4 | 60 |
| QP100MH | 4,400–6,000 | 4 | 30 |

The viscosities were determined on a Brookfield viscometer at 25° C. and are reported in centipoise. The various grades were dissolved in TB buffer. The polymer was dissolved in the buffer, at selected weight percentages, by vortexing the buffer and adding the powdered polymer rapidly. Within five minutes the solution viscosity increased to a high-viscosity state. The mixture was allowed to sit 24 hours at room temperature to insure complete dissolution.

C. Polyacrylamide Matrix

Acrylamide monomer (Bio-Rad Inc., Richmond, CA) was prepared as a 30% solution in deionized water. This was then combined with a 10x buffer concentrate (Tris-Glycine-SDS, #832-7603, Kodak Inc., Rochester, NY) and water to obtain various monomer concentrations. The acrylamide was polymerized by adding ammonium persulphate and tetraethylmethyl diamine. Once the catalysts were added the mixture was placed under nitrogen and allowed to cure for two hours at 25° C.

D. Matrix Pumping Procedure

Each of the above polymer matrix material was pumped into a fused silica capillary tube, typically a #TSP75/350 capillary tube obtained from Polymicro Technologies, Inc. (Phoenix, AZ). This tube has a 75 micron ID and was cut to 42 cm. Injection of the polymer matrix solutions into the into capillary tubes was done as follows. One gram of the finished matrix was placed with a spatula into a 5 cc syringe and then injected into a 5 cc stainless steel tube with a 0.125" OD and a 0.040" ID. The stainless steel tube was coupled to Model 140A high-pressure pump (from Applied Biosystems) at one tube end, and to the above capillary tube at the other end. Connections were with low dead volume fittings, such as connectors Part #U437 from Upchurch Scientific Inc. (Seattle, WA). The pump was filled with water and used to apply a pressure of between about 2,500–7500 psi to the in order to pump the matrix into the tube. The pressure was typically set to achieve a pumping rate of about 250 μL per minute.

EXAMPLE 2

Fractionation of Proteins on a Polyacrylamide Matrix

A mixture of proteins containing lactalbumin, molecular weight 14,200 daltons (0.1 mg/ml), lactalglobulin, molecular weight 17,500 daltons (0.1 mg/ml), trypsin inhibitor, molecular weight 20,000 daltons (0.1 mg/ml), and carbonic anhydrase, molecular weight 29,000 daltons (0.1 mg/ml) was prepared in the above TB buffer.

Capillary electrophoresis was carried out using an ABI Model 270 capillary electrophoresis system. The system includes a built-in high-voltage DC power supply capable of voltage settings up to 30 KV. The polyacrylamide matrix used was the 42 cm capillary tube prepared as in Example 1C, at polyacrylamine concentrations of 4.5, 7.5, and 10 weight percent.

The two reservoirs were filled with TB buffer. The protein sample was electrophoretically drawn into the tube for 1.5 seconds at 5 kV. The electrophoretic system was run at a voltage setting of about 9 kV (about 200 V/cm) through the run. UV detection was with a Kratos 783 UV detector designed for capillary tube detection. The detector output signal was integrated and plotted on an HP Model 3396A integrator/plotter.

The electropherogram obtained is shown in FIGS. 6A-6C for the 4.5, 7.5, and 10 weight percent polymers, respectively. The numbers above the major peaks (A-D) are electrophoresis times, in minutes. Total run time was about 30 minutes. As described above, the method effectively separated proteins in the range 14 to 30 kilodaltons at 7.5 and 10 weight percent polymer.

EXAMPLE 3

Fractionation of Nucleic Acid Fragments on a PEO Matrix

A. Effect of Polymer Molecular Weight

Capillary tubes with supported PEO matrices, at two different PEO molecular weights, were prepared as described in Example 1A. An oligonucleotide ladder (40mer to 60mer) obtained from Pharmacia (Bromma, Sweden) was prepared in TB buffer and introduced into each of the tubes, at the cathodic end, in the capillary electrophoresis system described in Example 2. The applied voltage was nine kilovolts and the detection wavelength was 260 nm. The electropherograms for the 900 kilodalton and 7,000 kilodaltons PEO polymers are shown in FIGS. 7A and 7B, respectively. As seen, the nucleic acid fragments are significantly better resolved in the higher molecular weight polymer matrix.

B. Effect of Polymer Concentration

Capillary tubes with supported PEO matrices, were prepared using the above WSR3030 PEO polymer (7 million average molecular weight), at polymer concentrations of 6% and 15%, substantially as described in Example 1A. A 40mer-60mer oligonucleotide ladder was fractionated on the supported matrices, substantially as described in Part A above. The applied voltage was nine kilovolts and the detection wavelength was 260 nm. The electropherograms for the 6% and 15% polymer solutions are shown in FIGS. 8A and 8B, respectively. As seen, the nucleic acid fragments are significantly better resolved in the more concentrated polymer matrix.

EXAMPLE 4

Fractionation of Nucleic Acid Fragments on an HEC Matrix

A. Effect of Polymer Molecular Weight

Capillary tubes with supported HEC matrices prepared from the QP-40, QP-300, and QP-4400 polymers described in Example 1B, to a final polymer concentration of 10 weight percent in TB buffer, as described in Example 1. The oligonucleotide ladder (40mer to 60mer) from Example 3 was introduced into each of the tubes, at the cathodic end, in the capillary electrophoresis system described in Example 2. The applied voltage was 9 kV and the detection wavelength was 260 nm. The electropherograms for the QP-40, QP-300, and QP-4400 HEC polymers are shown in FIGS. 9A, 9B, and 9C, respectively. It can be seen in the electropherograms that all three polymer matrices gave similar resolution at the same polymer concentration, despite the different polymer molecular weights.

B. Effect of Polymer Concentration

Capillary tubes with supported HEC matrices prepared from the QP-300 polymer described in Example 1B, at polymer concentrations in TB buffer of 3, 10, 15 and 25 weight percent QP-300. An oligonucleotide ladder (20 mer to 40mer) obtained from Pharmacia was introduced into each of the tubes, at the cathodic end, in the capillary electrophoresis system described above. The applied voltage was 9 kV and the detection wavelength was 260 nm. The electropherograms for the 3%, 10%, 15%, and 25% polymer matrices are seen in FIGS. 10A, 10B, 10C, and 10D, respectively.

EXAMPLE 5

Separation of Phosphorylated and Non-Phosphorylated Nucleic Acid Fragments

An HEC gel was formulated as described in Example 1B using QP4400H at a concentration of ten percent in TB buffer, and injected into a capillary tube. A set of polyadenylic acids (12-18 bases) was fractionated on the matrix under the electrophoretic conditions detailed in Example 3, with the results shown in FIG. 11A. As seen from the figure, all of the phosphorylated nucleotides are baseline resolved, but with shadow peaks.

When the same set of nucleotides in non phosphorylated form were fractionated under the same conditions, the electropherogram shown in FIG. 12B was obtained. The electropherogram is distinguished by the lack of shadow peaks, but otherwise resembles the FIG. 12A electropherogram.

When a mixture of roughly equal amounts of phosphorylated and non-phosphorylated nucelotides were fractionated under the same conditions, the electropherogram seen in FIG. 12C was obtained. It is clear from a comparison of the three FIG. 12 electropherograms that (a) the shadow peaks seen in FIG. 12A are non-phosphorylated contaminants and (b) the electrophoretic system is effective to resolve phosphorylated and non-phosphorylated nucleotide analogs.

EXAMPLE 6

Mixed Polymer Matrix

A mixed polymer solution containing both HEC and polyacrylamide was prepared from the following components:
- 0.5 g: QP3L
- 0.5 ml: TBE (5×conc.)
- 4.5 ml: Deionized Water
- 3.5 ml: 30% Acrylamide in Deionized Water The ingredients were mixed well and then catalyst was added as described in Example 1C to polymerize the acrylamide. The final percentage of HEC was about 5.5 by weight; of polyacrylamide, about 11.5 by weight. After curing the polymer mixture was injected into a capillary tube and a separation of a 40 mer to 60 mer oligonucleotide was performed. The electropherogram obtained is shown in FIG. 13.

Although the invention has been described with respect to exemplary supported matrices and methods of use, it will be appreciated that various modifications and changes may be made without departing from the invention.

It is claimed:

1. A supported matrix for use in electric field-induced separation of nucleic acids in a sample comprising:

a support containing an elongate separation chamber, and contained within said chamber, and filling the chamber substantially uniformly, an aqueous viscoelastic matrix characterized by:
(i) a water-soluble, substantially non-crosslinked polymer having a molecular weight of at least about 200,000 daltons and having a concentration in the matrix of between about 0.1 to 5 percent by weight, said polymer selected from the group consisting of polyvinyl alcohol and a water-soluble, hydroxylated cellulose compound, and
(ii) a viscosity of at least about 100,000 centipoise.

2. The matrix of claim 1 for use in separating nucleic acids wherein the polymer is a mixture of a first polymer selected from the group consisting of polyethylene oxide, polyacrylamide, and polymethacrylamide, and a second polymer selected from the group consisting of a water-soluble, hydroxylated cellulose compound and polyvinyl alcohol.

3. The matrix of claim 1, for use in isoelectric focusing, wherein the polymer matrix contains ampholyte species effective to establish a substantially continuous pH gradient over a selected pH range.

4. A method of electrophoretic separation of molecular component sin a sample comprising:
adding a sample to one end region of a support defining an elongate separation chamber which is filled, substantially uniformly, with an aqueous electrolyte-containing polymer matrix characterized by:
(i) a water-soluble, substantially non-crosslinked polymer having a molecular weight of at least 5–10 kilodaltons, and
(ii) a viscosity of at least 5,000 centipoise,
separating said components by applying an electric field across opposite end regions of the chamber, until a desired degree of electrophoretic separation of the components is achieved,
removing a selected region of the polymer matrix containing a separated sample component,
liquefying the removed region to form a low-viscosity liquid, and
isolating the sample component from the polymer in the liquid.

5. The method according to claim 4, wherein said liquefying is carried out by diluting the solution in an aqueous medium.

6. A method of fractionating a sample of nucleic acid components in the size range less than about 100 bases, comprising
adding said sample to one end region of a support defining an elongate separation chamber which is filled, substantially uniformly, with an aqueous electrolyte-containing polymer matrix characterized by:
(i) a mixture of polymers, one of which is selected from selected from the group consisting of polyethylene oxide, polyacrylamide, and polymethacrylamide, and another of which is selected from the group consisting of a water-soluble hydroxylated cellulose compound,
(ii) polymer molecular weights of molecular weight of at least about 100,000 daltons, and
(iii) a viscosity of at least about 100,000 centipoise, and
separating nucleic acid components by applying an electric field across opposite end regions of the chamber, until a desired degree of electrophoretic separation of the components is achieved.

7. The method of claim 6, wherein the polymer mixture contains at least about 5 weight percent of each of the polymers in the mixture.

8. The method of claim 6, for separation of oligonucleotides having sizes less than about 50 bases, wherein the polymer mixture has a viscosity, as measured by as measured by the pressure needed t pump the matrix through a 30 cm length of 75 $\mu$ capillary tube, at a flow rate of 100 $\mu$l/min, at room temperature, is at least about 3,000 psi.

9. A method of separating molecular components in a sample by isoelectric focusing comprising:
adding the sample to a matrix supported in an elongate separation chamber which is filled, substantially uniformly, with an aqueous ampholyte-containing polymer matrix characterized by:
(i) a water-soluble, substantially non-crosslinked polymer having a molecular weight of at least about 5–10 kilodaltons, and
(ii) a viscosity of at least 5,000 centipoise, and
separating said components by applying an electric field across opposite end regions of the chamber, until the ampholyte has equilibrated to produce a selected pH gradient across the end regions of the chamber, and the molecular components have migrated to their isoelectric points within the chamber,
removing a selected region of the polymer matrix containing a separated sample component,
liquefying the removed region to form a low-viscosity liquid, and
isolating the sample component from the polymer in the liquid.

10. The method of claim 9, wherein said liquefying is carried out by diluting the solution in an aqueous medium.

11. A method of electrophoretic separation of molecular components in a sample comprising:
adding a sample to one end region of an electrophoresis tube which is filled, substantially uniformly, with an aqueous electrolyte-containing polymer matrix characterized by:
(i) a water-soluble, substantially non-crosslinked polymer having a molecular weight of at least 5–10 kilodaltons, and
(ii) a viscosity of at least 5,000 centipoise,
separating said components by applying an electric field across opposite end regions of the tube, until a desired degree of electrophoretic separation of the components is achieved,
forming the matrix out of the tube, and
monitoring the matrix for the presence of discrete sample component bands as the matrix is forced from the tube.

12. A method of electrophoretic separation of oligonucleotides in a sample comprising:
adding a sample of to one end region of an electrophoresis tube which is filled, substantially uniformly, with an aqueous electrolyte-containing polymer matrix characterized by:
(i) a water-soluble, substantially non-crosslinked hydroxylated cellulose compound having a molecular weight of at least 5–10 kilodaltons, and
(ii) a viscosity of at least 5,000 centipoise, and
separating said components by applying an electric field across opposite end regions of the chamber, until a desired degree of electrophoretic separation of the components is achieved.

13. A method of electrophoretic separation of oligonucleotides in a sample comprising:
adding a sample to one end region of an electrophoresis tube which is filled, substantially uniformly, with an aqueous electrolyte-containing polymer matrix characterized by:
(i) a water-soluble, substantially non-crosslinked polymer mixture having a molecular weight of at least 5-10 kilodaltons, said polymer matrix comprising a first polymer selected from the group consisting of polyethylene oxide, polyacrylamide and polymethacrylamide and a second polymer selected from the group consisting of a water-soluble, hydroxylated cellulose compound and polyvinyl alcohol,
(ii) a viscosity of at least 5,000 centipoise, and
separating said components by applying an electric field across opposite end regions of the chamber, until a desired degree of electrophoretic separation of the components is achieved.

14. A method of electrophoretic separation of a phosphorylated low molecular weight nucleic acid component from its non-phosphorylated analog in a sample comprising:
adding a sample to one end region of an electrophoresis tube which is filled, substantially uniformly, with an aqueous electrolyte-containing polymer matrix characterized by:
(i) a viscosity of at least 5,000 centipoise, and
separating said components by applying an electric field across opposite end regions of the chamber, until a desired degree of electrophoretic separation of the components is achieved.

15. A method of separating molecular components in a sample by isoelectric focusing comprising:
adding the sample to a matrix supported in a tube which is filled, substantially uniformly, with an aqueous ampholyte-containing polymer matrix characterized by:
(i) a water-soluble, substantially non-crosslinked polymer having a molecular weight of at least about 5-10 kilodaltons, and
(ii) a viscosity of at least 5,000 centipoise,
separating said components by applying an electric field across opposite end regions of the tube, until the ampholyte has equilibrated to produce a selected pH gradient across the end regions of the tube, and the molecular components have migrated to their isoelectric points within the tube,
forcing the matrix out of the tube, and
monitoring the matrix for the presence of discrete sample component bands as the matrix is forced from the tube.

16. A method of preparing a supported, substantially homogeneous matrix for use in electric field-induced separation of nucleic acids in a sample comprising:
forming a viscoelastic, flowable aqueous polymer matrix characterized by:
(i) a water-soluble, substantially non-crosslinked polymer, having a molecular weight of at least about 5-10 kilodaltons,
(ii) a viscosity of at least about 5,000 centipoise, and
(iii) containing an electrolyte; and
pumping the polymer matrix, in its high-viscosity state, into an elongate separation chamber, to fill the chamber uniformly with the matrix, wherein the polymer is a hydroxylated polymer selected from the group consisting of a water-soluble hydroxylated cellulose compound and polyvinyl alcohol.

17. A method of preparing a supported, substantially homogeneous matrix for use in electric field-induced separation of nucleic acids in a sample comprising:
forming a viscoelastic, flowable aqueous polymer matrix characterized by:
(i) a water-soluble, substantially non-crosslinked polymer, having a molecular weight of at least about 5-10 kilodaltons,
(ii) a viscosity of at least about 5,000 centipoise, and
(iii) containing an electrolyte; and
pumping the polymer matrix, in its high-viscosity state, in to an elongate separation chamber, to fill the chamber uniformly with the matrix, wherein the polymer is a mixture of a first polymer selected from the group consisting of polyethylene oxide, polyacrylamide, and polymethacrylamide, and a second polymer selected from the group consisting of a water-soluble, hydroxylated cellulose compound and polyvinyl alcohol.

* * * * *

UNITED STATES PATENT AND TRADEMARK OFFICE
CERTIFICATE OF CORRECTION

PATENT NO. : 5,164,055
DATED : November 17, 1992
INVENTOR(S) : Robert S. Dubrow

Page 1 of 3

It is certified that error appears in the above-indentified patent and that said Letters Patent is hereby corrected as shown below:

Col. 2, line 49, delete "cur" and insert --cure--.

Col. 3, line 29, after "gradient" delete the dash ("-") and insert a period (--.--).

Col. 3, line 39, after "autoradiography" insert a comma (--,--).

Col. 5, line 15, change "isolated" to --isolation--.

Col. 5, line 18, after "6A" add a hyphen and the characters 6B (-- -6B --).

Col. 5, lines 25-26, delete "(6A)" and "(6B)" and insert --(7A)-- and --(7B)--.

Col. 5, line 43, delete "(10d)" and insert --(10D)--.

Col. 5, line 46, delete "and".

Col. 5, line 53, delete "electropherogram" and insert --electropherograms--.

Col. 6, line 7, before "preparing" delete "the".

Col. 6, line 47, after "polymer" insert --which--.

Col. 7, line 29, delete "ad" and insert --and--.

Col. 7, line 59, before "known-weight" delete "a".

Col. 10, line 2, delete "1".

Col. 10, end of line 14, delete "2" and insert --32--.

UNITED STATES PATENT AND TRADEMARK OFFICE
CERTIFICATE OF CORRECTION

PATENT NO. : 5,164,055
DATED : November 17, 1992
INVENTOR(S) : Robert S. Dubrow

It is certified that error appears in the above-indentified patent and that said Letters Patent is hereby corrected as shown below:

Col. 10, line 58, delete "allow" and insert --allows--.

Col. 11, line 8, between "$\mu l$" and "min" insert diagonal slash (--/--).

Col. 11, line 68, insert a period after "KV" (--.--)

Col. 12, line 14, insert a period (--.--) after "detection".

Col. 12, line 41, between "wintin" and "downstream" insert a period (--.--).

Col. 12, line 52, between "$\mu l$" and "minute" insert a diagonal slash (--/--).

Col. 12, line 52, delete "1,00" and insert --100--.

Col. 13, line 2, delete "can" and insert --and--.

Col. 13, line 15, delete "isolated" and insert --isolate--.

Col. 13, line 29, delete "transferee" and insert --transferred--

Col. 14, line 5, after "35,000" insert --to--.

Col. 15, line 2, before "900" delete "a".

Col. 15, line 43, delete "in Example" (second occurrence).

Col. 16, line 6, delete "as" and insert --is--.

Col. 16, line 66, after "met in" delete "a".

UNITED STATES PATENT AND TRADEMARK OFFICE
CERTIFICATE OF CORRECTION

PATENT NO. : 5,164,055
DATED : November 17, 1992
INVENTOR(S) : Robert S. Dubrow

It is certified that error appears in the above-indentified patent and that said Letters Patent is hereby corrected as shown below:

Col. 17, line 53, after "and a" delete "the".

Col. 18, line 29, delete "material" and inset --materials--.

Col. 18, line 34, after "into the" delete "into".

Col. 18, line 46, after "psi" delete "to the".

Col. 19, line 28, change "kilodaltons" to --kilodalton--.

Col. 20, line 34, delete "nucelotides" and insert --nucleotides--.

In Claim 6, Col. 21, line 58, after "from" delete "selected from".

In Claim 8, Col. 22, line 9, delete "as measured by" (second occurrence).

In Claim 11, Col. 22, line 53, delete "forming" and insert --forcing--.

Signed and Sealed this

Twenty-ninth Day of November, 1994

BRUCE LEHMAN

Attest:

Attesting Officer

Commissioner of Patents and Trademarks